United States Patent [19]
Okorodudu

[11] 3,986,967
[45] Oct. 19, 1976

[54] ORGANOPHOSPHORUS DERIVATIVES OF BENZOTRIAZOLE AND THEIR USE AS LOAD CARRYING ADDITIVES

[75] Inventor: Abraham O. M. Okorodudu, West Deptford, N.J.

[73] Assignee: Mobil Oil Corporation, New York, N.Y.

[22] Filed: Oct. 17, 1975

[21] Appl. No.: 623,279

[52] U.S. Cl. .............................. 252/49.9; 252/32.5; 260/308 B
[51] Int. Cl.$^2$ ........................................... C10M 1/10
[58] Field of Search ..................... 252/32.5, 49.9; 260/308 B

[56] References Cited
UNITED STATES PATENTS

| | | | |
|---|---|---|---|
| 3,553,131 | 1/1971 | Hepplewhite et al. | 252/49.9 |
| 3,677,943 | 7/1972 | Nnadi | 252/49.9 X |
| 3,819,647 | 6/1974 | Foley | 252/32.5 X |
| 3,844,957 | 10/1974 | Robinson et al. | 252/32.5 |
| 3,846,317 | 11/1974 | Lintzenich | 252/49.9 X |
| 3,868,376 | 2/1975 | Hotten | 252/49.9 X |

FOREIGN PATENTS OR APPLICATIONS

| | | | |
|---|---|---|---|
| 243,032 | 9/1960 | Australia | 260/308 B |

*Primary Examiner*—D. Horwitz
*Assistant Examiner*—Andrew H. Metz
*Attorney, Agent, or Firm*—Charles A. Huggett; Raymond W. Barclay; Claude E. Setliff

[57] ABSTRACT

Lubricants are stabilized with an organophosphorus-benzotriazole product, resulting in the ability to support higher load factors in the lubricated system.

14 Claims, No Drawings

ORGANOPHOSPHORUS DERIVATIVES OF BENZOTRIAZOLE AND THEIR USE AS LOAD CARRYING ADDITIVES

BACKGROUND OF THE INVENTION

1. Field of the Invention

The invention relates to new lubricant additives effective as load carrying agents. More particularly, the load carrying agents are certain new organophosphorusbenzotriazole derivatives.

2. Discussion of the Prior Art

Benzotriazole is a well-known additive to lubricants, to power train fluids and to anti-freeze solutions. It is known, for example that benzotriazole can be utilized in a lubricating oil as a corrosion inhibitor. It can also be used as a copper deactivator in an anti-freeze solution (U.S. Pat. No. 3,597,353). Benzotriazole has been mixed with other materials such as phenol, an amine, a polyhydroxyquinone, an amine salt and an organic phosphite to produce an anti-oxidant for polyglycol based lubricants.

The use of phosphorus compounds, per se, as EP agents in lubricants is well known. The use of organic phosphorus compounds in combination with, for example, hindered phenols to produce load carrying additives for lubricants is known from U.S. Pat. No. 3,471,404. So far as is known, however, no art is available which suggests the reaction product of benzotriazole with an organophosphorus compound and its use as a load carrying agent.

Although benzotriazole does per se have such diversified activity in lubricant compositions, its solubility in such lubricant is extremely limited. There has accordingly been considerable work directed to overcoming the effect of this limited solubility without sacrificing its utility.

SUMMARY OF THE INVENTION

The invention provides compounds of the formula:

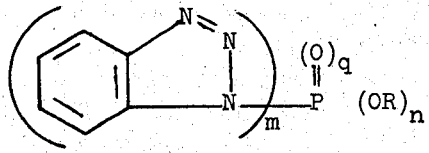

wherein $m$ is 1 or 2, $n$ is 1 or 2, their sum being 3, $q$ is zero or 1 and R is a hydrocarbyl group having from 1 to 32 carbon atoms. The group includes (1) aromatic members having 6 to 14 carbon atoms and the alkyl-substituted members thereof, the alkyl containing from 1 to 18 carbon atoms and (2) aliphatic groups containing 1 to 32 carbon atoms, especially alkyl groups. Where $n$ is 2, one R can be aliphatic and the other aryl as defined hereinabove. The invention also provides lubricant compositions containing a major amount of lubricant and a load carrying amount of the herein defined compound.

DESCRIPTION OF SPECIFIC EMBODIMENTS

The compounds of this invention can be prepared in a number of ways. One method involves the reaction of benzotriazole with an organophosphorochlorido compound, in accordance with the following:

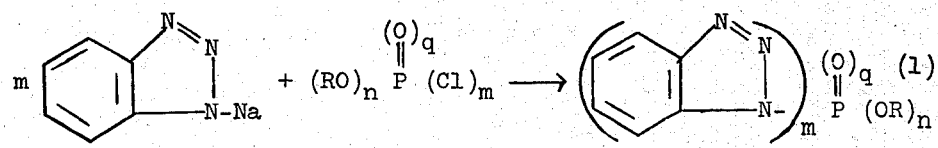

Another method employs benzotriazole in reactions with organic derivatives of phosphonous, phosphinous, phosphonic and phosphinic acids in the presence of a halogenated hydrocarbon, e.g. carbon tetrachloride. The reaction is shown as follows:

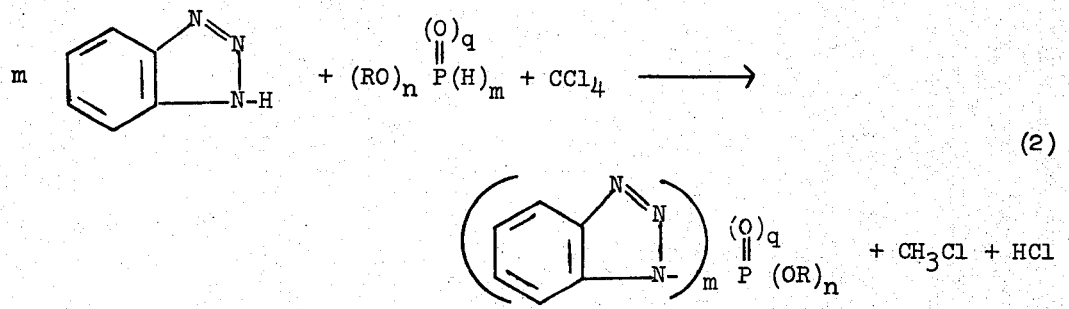

In these, R, $m$, $n$ and $q$ have the meaning defined hereinabove.

One method of preparation according to (1) above involves the addition of a diorgano phosphorochloridate to an equimolar amount of a suspension of the sodium salt of benzotriazole in benzene at ambient temperatures. Following the addition and resulting exothermic reaction, the mixture is heated for from 1 to 6 hours at 55°–75° C or at reflux, cooled and treated with sodium chloride solution and benzene. In cases where emulsion resulted, a separation of phases was effected by the addition of a minor amount of butanol. The organic extract is then stripped of solvent under vacuum to give the product.

In method 2, a solution of benzotriazole in pyridine is added, dropwise to an equimolar amount of diorganophosphonate in carbon tetrachloride while heating slowly to reflux. After refluxing for 1 to 10 hours, the mixture is cooled and treated with carbon tetrachloride and water. The organic extract is stripped of solvent under vacuum, to give the product.

As has already been stated, the R group in the phosphatic reactant is hydrocarbyl group containing up to 32 carbon atoms, which can be aromatic, alkyl-substituted aromatic or alkyl. The aromatic groups include phenyl, naphthyl and anthryl, and those members substituted with a $C_1$–$C_{18}$ alkyl. Such alkyl groups include methyl, butyl, octyl, decyl, dodecyl, tetradecyl, octadecyl and the like, and it will be understood that the mention of each of these is a disclosure of its attachment to each of the aromatic groups mentioned and the incorporation of the alkylaromatic compound into the various final products contemplated by this invention. Finally, the alkyl group (R) can also have from 1 to 32 carbon atoms and includes methyl, ethyl, hexyl, nonyl, tetradecyl and octadecyl, eicosyl, pentacosyl, triacontyl and dotriacontyl. Here again, the disclosure of each of these groups is a disclosure of their incorporation in all the various final products of this invention.

The products of this invention are effective in fluid compositions in which the lubricant base is a petroleum product, such as a mineral lubricating oil, or a synthetic fluid. Such synthetic fluids include synthetic hydrocarbon oils derived from long chain alkanes or olefin polymers, ester oils obtained from polyhydric alcohols and monocarboxylic acids or monohydric alcohols and polycarboxylic acids. Also, the lubricants contemplate greases made from the named classes of fluids.

The concentration of additive may vary from about 0.05 to about 10% by weight. Optimum performance characteristics are evidenced by lubricants containing from about 0.25% to about 2% by weight of the additives of this invention, and this is the preferred range of concentration.

Having defined the invention in general terms, the following Examples are offered as illustrations.

EXAMPLE 1

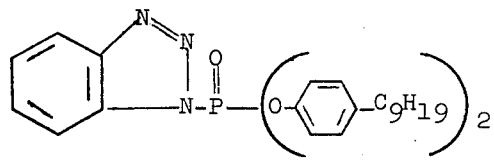

To a rapidly stirred slurry of 0.5 mole of the sodium salt of benzotriazole in 300 ml of benzene was added, dropwise, 0.5 mole of di(nonylphenyl) phosphorochloridate. The reaction system was protected from moisture.

After the addition, and after the initial exothermic reaction had subsided, the mixture was heated at 60° C for 1½ hours and then was cooled to room temperature. The reaction mass was treated with 200 ml of benzene and 200 ml of saturated sodium chloride solution. The organic portion was separated, dried over magnesium sulfate and stripped of solvent. A light brown liquid product was obtained, containing 4.7% phosphorus (calculated 5.1%) and 6.1% nitrogen (calculated 6.9%).

EXAMPLE 2

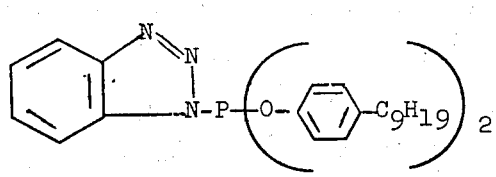

This compound was prepared as outlined in Example 1, except that the *phosphorochlorodite* was used. The product obtained contained 7.5% of phosphorus (calculated 7.6%) and 10.3% of nitrogen (calculated 10.3%).

EXAMPLE 3

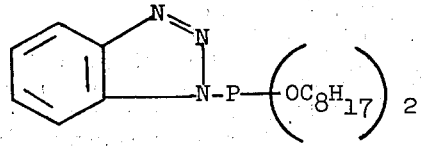

EXAMPLE 4

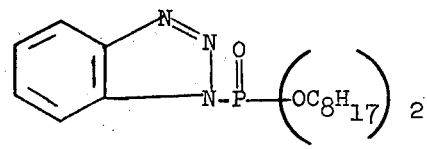

EXAMPLE 5

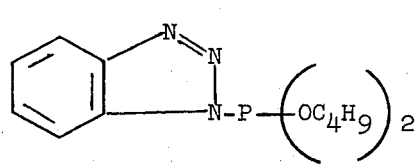

EXAMPLE 6

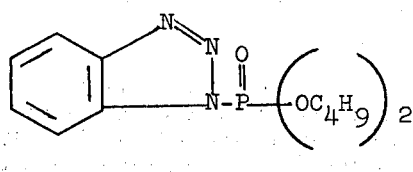

The compounds of Examples 3–6, inclusive, were made using substantially the same steps as defined in Example 1, employing the appropriate reagents.

EVALUATION OF PRODUCTS

The additives described hereinabove were evaluated in the Shell 4-Ball Wear Test using ½ in. 52100 Steel Balls at a load of 60 Kg and for 30 minutes under the conditions set forth in Table I below. The oil used was an 80/20 mixture of a 150 second solvent paraffinic bright mineral oil and a 200 second solvent paraffinic neutral mineral oil.

TABLE I

| Additive | Conc. Wt.% | Temp. °F | SCAR DIAMETER SPEED | | | |
|---|---|---|---|---|---|---|
| | | | 500 | 1000 | 1500 | 2000 |
| Base Stock | 100 | Room | 0.50 | 0.60 | 0.88 | 2.34 |
| | | 200 | 0.60 | 1.06 | 1.86 | 2.23 |
| | | 390 | 1.0 | 1.31 | 2.08 | — |
| Example 1 | 1 | 200 | 0.40 | 0.50 | 0.50 | 0.60 |
| | | 390 | 0.50 | 0.60 | 0.65 | 0.80 |
| Example 2 | 1 | 200 | 0.50 | 0.50 | 0.50 | 0.60 |
| | | 390 | 0.50 | 0.50 | 0.60 | 0.60 |
| Example 3 | 1 | 200 | 0.40 | 0.50 | 0.60 | 0.60 |
| | | 390 | 0.50 | 1.10 | 0.60 | 0.65 |
| Example 4 | 1 | 200 | 0.50 | 0.60 | 0.60 | 0.80 |
| | | 390 | 0.60 | 0.90 | 1.0 | 1.10 |
| Example 5 | 1 | 200 | 0.50 | 0.50 | 0.50 | 0.50 |
| | | 390 | 0.50 | 0.60 | 0.75 | 1.10 |
| Example 6 | 1 | 200 | 0.50 | 0.60 | 0.50 | 0.50 |
| | | 390 | 0.60 | 0.50 | 0.60 | 0.70 |
| Example 6* | 1 | 200 | 0.50 | 0.60 | 0.70 | 0.80 |
| | | 390 | 0.50 | 1.0 | 0.70 | 0.80 |

*Repeat

I claim:

1. A compond of the formula:

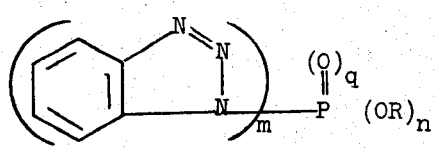

wherein $m$ is 1 or 2, $n$ is 1 or 2, their sum being 3, $q$ is zero or 1 and R is a hydrocarbyl group having from 1 to 32 carbon atoms.

2. The compound of claim 1 wherein $m$ is 1, $n$ is 2, $q$ is 1 and R is

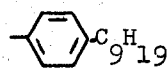

3. The compound of claim 1 wherein $m$ is 1, $n$ is 2, $q$ is zero and R is

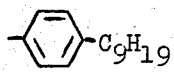

4. The compound of claim 1 wherein $m$ is 1, $n$ is 2, $q$ is zero and R is $-C_8H_{17}$.

5. The compound of claim 1 wherein $m$ is 1, $n$ is 2, $q$ is 1 and R is $-C_8H_{17}$.

6. The compound of claim 1 wherein $m$ is 1, $n$ is 2, $q$ is zero and R is $-C_4H_9$.

7. The compound of claim 1 wherein $m$ is 1, $n$ is 2, $q$ is 1 and R is $-C_4H_9$.

8. A lubricant composition comprising a major amount of an oil of lubricating viscosity or greases thereof and a load carrying amount of a compound of the formula:

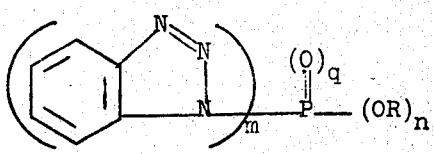

wherein $m$ is 1 or 2, $n$ is 1 or 2, their sum being 3, $q$ is zero or 1 and R is a hydrocarbyl group having from 1 to 32 carbon atoms.

9. The composition of claim 8 wherein $m$ is 1, $n$ is 2, $q$ is 1 and R is

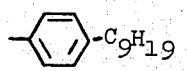

10. The composition of claim 8 wherein $m$ is 1, $n$ is 2, $q$ is zero and R is

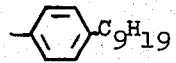

11. The composition of claim 8 wherein $m$ is 1, $n$ is 2, $q$ is zero and R is $-C_8H_{17}$.

12. The composition of claim 8 wherein $m$ is 1, $n$ is 2, $q$ is 1 and R is $-C_8H_{17}$.

13. The composition of claim 8 wherein $m$ is 1, $n$ is 2, $q$ is zero and R is $-C_4H_9$.

14. The composition of claim 8 wherein $m$ is 1, $n$ is 2, $q$ is 1 and R is $-C_4H_9$.

* * * * *